United States Patent [19]

Esrock

[11] Patent Number: 4,984,984

[45] Date of Patent: Jan. 15, 1991

[54] DENTAL TOOL AND NOZZLE THEREFOR

[76] Inventor: Bernard S. Esrock, 320 Dungate, Chesterfield, Mo. 63017

[21] Appl. No.: 221,028

[22] Filed: Jul. 18, 1988

[51] Int. Cl.$^5$ ............................................. A61C 3/02
[52] U.S. Cl. ................................... 433/88; 55/439
[58] Field of Search ................ 433/80, 126, 88, 82, 433/125; 51/439

[56] References Cited

U.S. PATENT DOCUMENTS

| | | | |
|---|---|---|---|
| 3,254,646 | 8/1962 | Staunt et al. | 128/224 |
| 3,698,088 | 10/1972 | Austin, Jr. | 433/80 |
| 3,874,083 | 4/1975 | Buckley | 433/80 |
| 3,882,638 | 5/1975 | Black | 51/12 |
| 3,972,123 | 8/1976 | Black | 32/58 |
| 4,026,025 | 5/1977 | Hunt | 433/80 |
| 4,068,664 | 1/1978 | Sharp et al. | 433/91 |
| 4,108,178 | 8/1978 | Betush | 433/80 |
| 4,149,315 | 4/1979 | Page, Jr. et al. | 32/22 |
| 4,174,571 | 11/1979 | Gallant | 433/216 |
| 4,184,258 | 1/1980 | Barrington et al. | 433/88 |
| 4,214,871 | 7/1980 | Arnold | 433/216 |
| 4,248,589 | 2/1981 | Lewis | 433/80 |
| 4,266,815 | 5/1981 | Cross | 604/905 |
| 4,412,402 | 12/1983 | Gallant | 433/88 |
| 4,462,803 | 7/1984 | Landgraf et al. | 433/88 |
| 4,487,582 | 12/1984 | Warris | 433/88 |
| 4,494,932 | 1/1985 | Rzewinski | 433/88 |
| 4,495,575 | 1/1985 | Mabille | 433/88 |
| 4,522,597 | 6/1985 | Gallant | 433/216 |
| 4,595,365 | 6/1986 | Edel et al. | 433/216 |
| 4,675,004 | 6/1987 | Hadford et al. | 604/44 |
| 4,676,749 | 6/1987 | Mabille | 433/88 |
| 4,680,026 | 7/1987 | Weightman et al. | 433/84 |
| 4,696,644 | 9/1987 | Goof | 433/125 |
| 4,696,645 | 9/1987 | Saupe et al. | 433/125 |

*Primary Examiner*—Cary E. Stone
*Attorney, Agent, or Firm*—Senniger, Powers, Leavitt & Roedel

[57] ABSTRACT

A nozzle for the simultaneous discharge of first and second fluids through a distal end thereof and for attachment to the hand piece of a dental tool comprising sources of the first and second fluids. The nozzle comprises first and second conduits and coupling means for removably coupling the nozzle to the hand piece. The first and second conduits have coaxial intake ports for fluid communication with the sources of the first and second fluids and coaxial discharge ports at the distal end of the nozzle for discharging the first and second fluids. The first conduit is contained at least partially within the second conduit and the discharge ports are proximately located with respect to one another. Upon coupling of the nozzle to the hand piece, the first conduit is automatically aligned with and connected to the source of the first fluid to enable quick connection and disconnection of the nozzle to the hand piece.

17 Claims, 2 Drawing Sheets

DENTAL TOOL AND NOZZLE THEREFOR

BACKGROUND OF THE INVENTION

This invention relates to a nozzle for use with a dental tool, and more particularly to a removable nozzle comprising coaxial conduits for delivering first and second fluids from a distal end thereof.

An air polisher is a type of dental tool used for cleaning teeth by spraying a cleansing mixture of water, air, and a soluble abrasive material against the teeth. Typical air polishers have an elongate hand piece for ease of handling and a nozzle at one of the ends thereof. The cleansing mixture flows through internal tubes within the hand piece and out of the nozzle in a stream which is directed against the teeth by the dental tool operator.

A problem encountered with such a nozzle is the difficulty in readily removing it from the hand piece for cleaning and sterilization. The nozzle must be unscrewed from the hand piece and then disconnected from the internal tubes within the hand piece. Additionally, cleaning and sterilizing such a nozzle is time consuming. Another problem encountered with such a nozzle is that the operator cannot vary the angle of the discharge streams to allow for easier access to hard to reach areas of the mouth.

SUMMARY OF THE INVENTION

Among the several objects of this invention may be noted the provision of an improved nozzle of the above-described type which is readily removable from a hand piece of a dental tool; the provision of such a nozzle which can be constructed inexpensively; the provision of such a nozzle which is disposable; and the provision of such a nozzle which is bendable by the user to vary the angle of the discharge streams with respect to the hand piece.

Briefly, therefore, the present invention is directed to a nozzle for the simultaneous discharge of first and second fluids through a distal end thereof and for attachment to the hand piece of a dental tool comprising sources of the first and second fluids. The nozzle comprises first and second conduits and coupling means for removably coupling the nozzle to the hand piece. The first and second conduits have coaxial intake ports for fluid communication with the sources of the first and second fluids and coaxial discharge ports at the distal end of the nozzle for discharging the first and second fluids. The first conduit is contained at least partially within the second conduit and the discharge ports are proximately located with respect to one another. Upon coupling of the nozzle to the hand piece, the first conduit is automatically aligned with and connected to the source of the first fluid to enable quick connection and disconnection of the nozzle to the hand piece.

The invention is further directed to a dental tool adapted for the simultaneous discharge of first and second fluids through a distal end thereof. The dental tool comprises a hand piece and a nozzle. The hand piece has means for providing the first and second fluids and additionally has means for coupling to the nozzle. The nozzle has means for coupling to the hand piece, first and second conduits with coaxial intake ports for fluid communication with the first and second tubes of the hand piece, and coaxial discharge ports proximately located at a distal end of the nozzle for discharging the first and second fluids. The first conduit is contained at least partially within the second conduit. Upon coupling the nozzle to the hand piece, the first conduit is automatically aligned with and connected to the means for providing the first fluid to enable quick connection and disconnection of the nozzle to the hand piece.

Other objects and features will be in part apparent and in part pointed out hereinafter.

BRIEF DESCRIPTION OF THE DRAWINGS

FIG. 3 is an end view of the nozzle; and

FIG. 4 is a longitudinal section view of an alternative embodiment of a nozzle of this invention.

Corresponding reference characters indicate corresponding parts throughout the several views of the drawings.

DESCRIPTION OF THE PREFERRED EMBODIMENT

Figure 1:
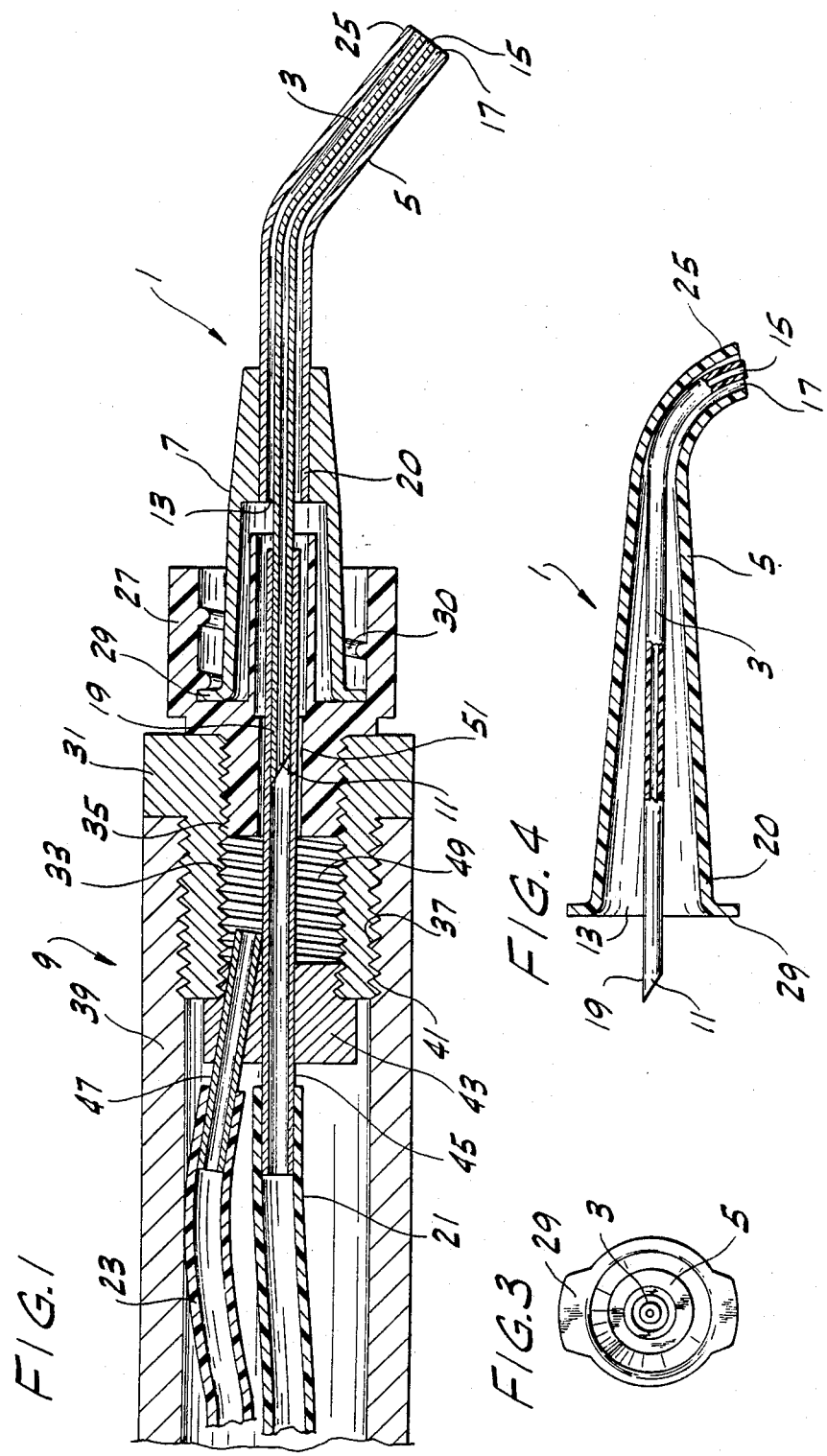
FIG. 1 is a longitudinal section view of a nozzle attached to the hand piece of a dental tool.
Figure 2:
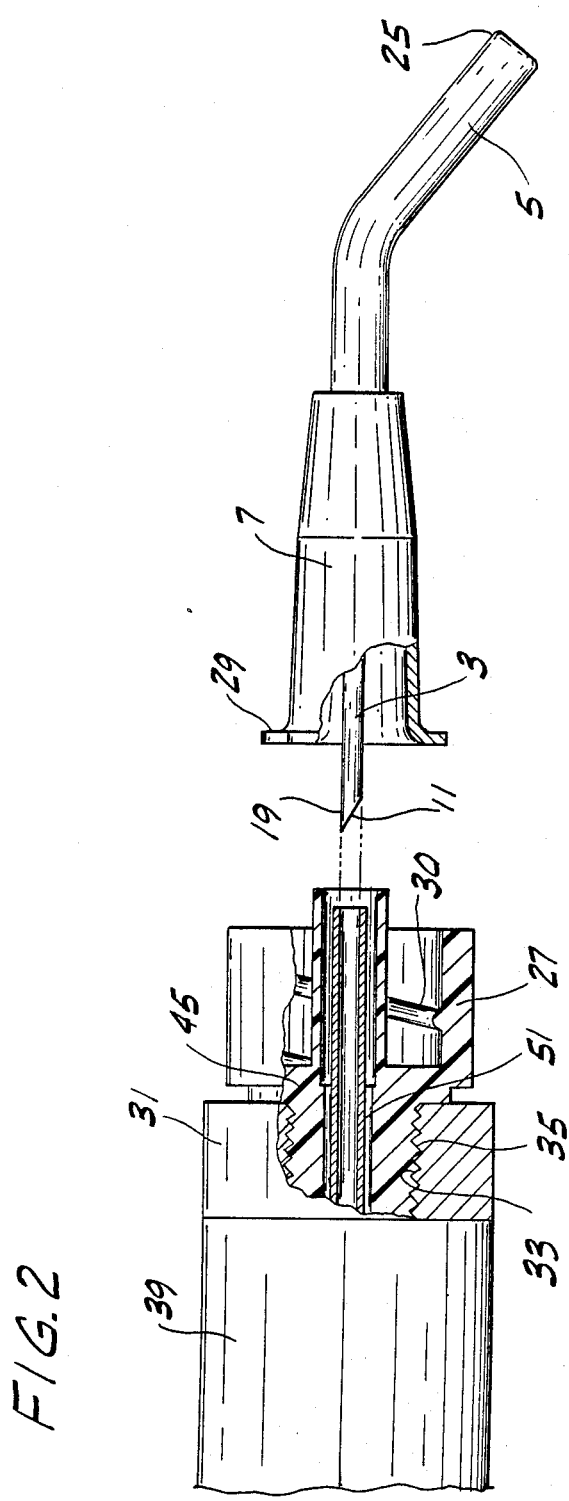
FIG. 2 is a longitudinal view, in partial section, of the nozzle and hand piece of FIG. 1 detached from each other.

Referring to FIGS. 1-3, there is generally indicated at 1 a nozzle of this invention. The nozzle 1 is adapted for delivering a mixed stream of first and second fluids against teeth of a patient to clean the teeth. The nozzle 1 comprises first and second coaxial conduits 3, 5 and a male fitting 7 for removably connecting the nozzle 1 to the hand piece 9 of a dental tool. The conduits have coaxial intake ports 11, 13 and coaxial discharge ports 15, 17. The proximal end 19 of the first conduit 3 extends longitudinally from the proximal end 20 of the second conduit 5 and the discharge ports 15, 17 of the conduits are proximately located with respect to each other. The hand piece 9 has a first flexible tube 21 for directing an abrasive laden air stream (e.g., air and sodium bicarbonate) to the first conduit 3, and a second flexible tube 23 for directing a liquid stream (e.g., water) to the second conduit 5. Thus, the two streams flow from the flexible tubes, through the conduits and are discharged through the distal end 25 of the nozzle 1.

The nozzle 1 is releasably connected to the hand piece 9 by quick connect fasteners or fittings. A male quick-connect fitting 7 at the proximal end of the nozzle 1 is adapted for interconnection with a female quick-connect fitting 27 at the distal end of the hand piece 9. The male fitting 7 and the female fitting 27 constitute means for releasably coupling the nozzle 1 to the hand piece 9. Preferably, the quick-connect fittings are Luer-type fittings such as those manufactured by Value Plastics, Inc., Ft. Collins, Colo. As shown in FIGS. 2 and 3, a substantially oblong-shaped flange 29 extends radially outwardly from the proximal end of the male fitting 7 and is adapted for engagement with an internal screw thread 30 in the female fitting 27. With fittings of this type, the nozzle 1 can be connected to or removed from the hand piece 9 by merely turning the nozzle 1 approximately one-fourth of a revolution with respect to the hand piece 9.

The hand piece 9 includes an adapter 31 for securing the female fitting 27 to the housing 39 of the hand piece 9. The adapter has an internal screw thread 33, an external screw thread 37, a base plug 43, and a central void 49 defined by the internal screw thread 33. The internal screw thread 33 is adapted for interconnection with an external screw thread 35 on the female fitting 27 and the external screw thread 37 of the adapter 31 is adapted for interconnection with an internal screw thread 41 in the housing 39. A first rigid tube 45 is coaxially disposed within the hand piece 9 and secured to the plug 43. The first rigid tube 45 is adapted for being coupled at one of its ends to the first flexible tube 21 and at its other end to the first conduit 3 to enable fluid communication between the first flexible tube 21 and the first conduit 3. The first conduit 3 is dimensioned for sliding into the first rigid tube 45 and coupled thereto by friction such that insertion of the male fitting 7 into the female fitting 27 causes the first conduit 3 to automatically align with and be inserted into the first rigid tube 45. A second rigid tube 47, extending through and secured to the plug 43, has a proximal end adapted for coupling to the second flexible tube 23 and a distal end extending into the central void 49 of the adapter 31. The first rigid tube 45 and the female fitting 27 are radially interspaced to define a cylindrical void 51 having a substantially annular cross section. In this arrangement, fluid may flow from the second flexible tube 23 to the second conduit 5 via the second rigid tube 47, central void 49, and cylindrical void 51.

Preferably the conduits 3, 5 are curved (or bent) to permit discharge of the fluids at oblique angles with respect to the hand piece 9; this enables a user to direct the fluids to hard to reach locations of a patient's teeth. Although the conduits are shown (for ease of understanding) as not contacting one another, it is to be understood that they do contact each other in the proximity of the bend. Bending of the conduits causes the first conduit 3 to be constrained within the second conduit 5 without a need for bonding the first conduit 3 to the second conduit 5. Additionally, the conduits may be formed of a bendable or ductile material so that a user can bend them to vary the angle which the discharged streams make with respect to the longitudinal axis of the hand piece.

Because of the geometric simplicity of the nozzle 1, the expense of manufacturing it is much less than that of prior art nozzles. Since the nozzle 1 can be manufactured inexpensively, it can be disposable, thus eliminating the need to clean and sterilize it after use.

FIG. 4 shows an alternative preferred embodiment of the nozzle 1. For convenience, corresponding parts are numbered identically as those parts shown in FIGS. 1-3. In the alternative preferred embodiment, the second conduit 5 is integrally formed with the Luer-type male fitting.

In view of the above, it will be seen that the several objects of the invention are achieved and other advantageous results attained.

As various changes could be made in the above constructions without departing from the scope of the invention, it is intended that all matter contained in the above description or shown in the accompanying drawing shall be interpreted as illustrative and not in a limiting sense.

What is claimed is:

1. A removable nozzle for the simultaneous discharge of first and second fluids through a distal end of the nozzle and for attachment to the hand piece of a dental tool comprising sources of the first and second fluids, the nozzle comprising:

first and second conduits having coaxial intake ports for fluid communication with the sources of the first and second fluids and coaxial discharge ports at the distal end of the nozzle for discharging the first and second fluids, the first conduit being contained at least partially within the second conduit and the conduits being bent to constrain the first conduit in the second conduit without bonding the conduits together, the discharge ports of the conduits being proximately located with respect to one another, and coupling means for releasably coupling the nozzle to the hand piece, wherein upon coupling the nozzle to the hand piece the first conduit is automatically aligned with and connected to the source of the first fluid to enable quick connection and disconnection of the nozzle to the hand piece.

2. A nozzle in accordance with claim 1 wherein one of the first and second conduits is adapted to transport abrasive laden air and the other conduit is adapted to transport a liquid.

3. A nozzle in accordance with claim 1 wherein the first and second conduits are curved to permit discharge of the fluids at oblique angles with respect to the hand piece.

4. A nozzle in accordance with claim 1 wherein the first and second conduits are constructed of a bendable material to enable bending of the conduits.

5. A nozzle in accordance with claim 1 wherein the coupling means comprises a Luer-type fastener secured to the second conduit and adapted for interconnection with the hand piece.

6. A nozzle in accordance with claim 1 wherein the coupling means comprises a Luer-type fastener integrally formed with the second conduit.

7. An improved dental tool of the type adapted to deliver a mixed stream of two fluids to teeth of a patient, the dental tool including a nozzle and a hand piece with the nozzle having first and second conduits, a proximal end, and a distal end, and the hand piece adapted for delivering a first fluid stream through a downstream end of the hand piece to the proximal end of the nozzle and through the first conduit and for delivering a second fluid stream through a downstream end of the hand piece to the proximal end of the nozzle and through the second conduit, the improvement comprising:

matable male and female Luer-type connectors for removably connecting the nozzle to the hand piece, wherein one of the connectors is secured to the proximal end of the second conduit and the other connector is secured to the downstream end of the hand piece so that when the connectors are mated the first conduit communicates with the first fluid stream and the second conduit communicates with the second fluid stream, said first fluid stream being delivered to the first conduit by a tube in the hand piece, said first conduit being engageable with said tube.

8. A dental tool in accordance with claim 7 wherein the first and second conduits comprise coaxial intake ports adjacent the proximal end and coaxial discharge ports adjacent the distal end, wherein the first conduit is contained at least partially within the second conduit and the discharge ports of the conduits are proximately located with respect to one another, and wherein the first and second conduits are adapted for fluid communication with the first and second fluid streams, respectively, for discharging the fluid streams from the distal end of the nozzle.

9. A dental tool in accordance with claim 8 wherein one of the conduits is adapted to transport an abrasive laden air stream and the other conduit is adapted to transport a liquid stream.

10. A dental tool in accordance with claim 8 wherein the first and second conduits are curved for discharging the fluid streams at an oblique angle with respect to the longitudinal axis of the hand piece.

11. A nozzle in accordance with claim 10 wherein the curvature of the conduits constrains the first conduit within the second conduit.

12. A dental tool in accordance with claim 7 wherein the nozzle is constructed of a bendable material for varying the angle which the ejected streams make with respect to the longitudinal axis of the hand piece.

13. A dental tool adapted for the simultaneous discharge of first and second fluids through a distal end thereof comprising a hand piece and a nozzle, the hand piece having means for providing the first and second fluids and means for coupling to the nozzle, the nozzle having means for coupling to the hand piece, first and second conduits with coaxial intake ports for fluid communication with the first and second tubes of the hand piece and coaxial discharge ports proximately located at a distal end of the nozzle for discharging the first and second fluids, the first conduit being contained at least partially within the second conduit, the conduits having sufficient curvature to constrain the first conduit within the second conduit, wherein upon coupling the nozzle to the hand piece, the first conduit is automatically aligned with and connected to the means for providing the first fluid to enable quick connection and disconnection of the nozzle to the hand piece.

14. A dental tool in accordance with claim 13 wherein one of the first and second conduits is adapted to transport abrasive laden air and the other conduit is adapted to transport a liquid.

15. A dental tool in accordance with claim 13 wherein the first and second conduits are curved to permit discharge of the fluids at oblique angles with respect to the hand piece.

16. A dental tool in accordance with claim 13 wherein the first and second conduits are constructed of a bendable material to enable bending of the conduits.

17. A dental tool in accordance with claim 13 wherein the hand piece coupling means and the nozzle coupling means comprise matable male and female Luer-type fastener means.

* * * * *